(12) United States Patent
Daly

(10) Patent No.: US 9,290,437 B2
(45) Date of Patent: Mar. 22, 2016

(54) ESTERS WITH ANTIMICROBIAL, BIORESISTANT AND FUNGAL RESISTANT PROPERTIES

(71) Applicant: Thomas Daly, Arlington Heights, IL (US)

(72) Inventor: Thomas Daly, Arlington Heights, IL (US)

( * ) Notice: Subject to any disclaimer, the term of this patent is extended or adjusted under 35 U.S.C. 154(b) by 0 days.

(21) Appl. No.: 14/558,122

(22) Filed: Dec. 2, 2014

(65) Prior Publication Data

US 2015/0094480 A1    Apr. 2, 2015

Related U.S. Application Data

(60) Continuation of application No. 14/293,054, filed on Jun. 2, 2014, now Pat. No. 8,901,332, which is a division of application No. 13/741,518, filed on Jan. 15, 2013, now Pat. No. 8,742,151, which is a continuation of application No. 13/351,512, filed on Jan. 17, 2012, now abandoned, which is a continuation of application No. 12/965,252, filed on Dec. 10, 2010, now abandoned, which is a division of application No. 12/287,726, filed on Oct. 10, 2008, now abandoned, which is a continuation-in-part of application No. 11/800,569, filed on May 7, 2007, now Pat. No. 7,439,376, which is a continuation-in-part of application No. 10/603,356, filed on Jun. 25, 2003, now abandoned.

(60) Provisional application No. 60/392,007, filed on Jun. 26, 2002.

(51) Int. Cl.
| | |
|---|---|
| *C07C 205/51* | (2006.01) |
| *A01N 37/12* | (2006.01) |
| *B01D 19/04* | (2006.01) |
| *C10M 105/56* | (2006.01) |
| *C10M 133/32* | (2006.01) |
| *C11D 1/66* | (2006.01) |
| *C11D 7/32* | (2006.01) |
| *C23F 11/14* | (2006.01) |
| *C07C 229/12* | (2006.01) |
| *C07C 205/50* | (2006.01) |
| *C07F 7/08* | (2006.01) |
| *C08G 77/388* | (2006.01) |
| *C08G 77/392* | (2006.01) |

(52) U.S. Cl.
CPC .............. *C07C 205/51* (2013.01); *A01N 37/12* (2013.01); *B01D 19/0413* (2013.01); *C07C 205/50* (2013.01); *C07C 229/12* (2013.01); *C07F 7/0854* (2013.01); *C08G 77/388* (2013.01); *C08G 77/392* (2013.01); *C10M 105/56* (2013.01); *C10M 133/32* (2013.01); *C11D 1/667* (2013.01); *C11D 7/32* (2013.01); *C23F 11/145* (2013.01); *C23F 11/147* (2013.01); *C10M 2215/003* (2013.01); *C10M 2215/202* (2013.01); *C10N 2230/16* (2013.01); *C10N 2230/18* (2013.01); *C10N 2240/401* (2013.01)

(58) Field of Classification Search
USPC .................................................. 554/223, 110
See application file for complete search history.

(56) References Cited

U.S. PATENT DOCUMENTS

| | | | |
|---|---|---|---|
| 2,185,297 A | 1/1940 | Gloor | 560/264 |
| 2,374,484 A | 4/1945 | Haas et al. | 560/264 |
| 2,402,776 A * | 6/1946 | Robinette, Jr. | 8/115.6 |
| 3,592,892 A | 7/1971 | Nosler et al. | |
| 4,263,424 A | 4/1981 | Buckley | |
| 4,576,625 A | 3/1986 | Norden et al. | |
| 8,742,151 B2 * | 6/2014 | Daly | 554/223 |

OTHER PUBLICATIONS

All references, supplied documents, foreign documents and other art from parent U.S. Appl. No. 13/741,518, filed Jan. 15, 2013, U.S. Appl. No. 13/351,512, filed Jan. 17, 2012; U.S. Appl. No. 12/965,252, filed Dec. 10, 2010; U.S. Appl. No. 12/287,726, filed Oct. 10, 2008; U.S. Appl. No. 11/800,569, filed May 7, 2007; U.S. Appl. No. 10/603,356, filed Jun. 25, 2003; U.S. Appl. No. 60/392,007, filed Jun. 26, 2002. U.S. Appl. No. 14/293,054.

* cited by examiner

*Primary Examiner* — Kristin Vajda
(74) *Attorney, Agent, or Firm* — Clifford H. Kraft

(57) ABSTRACT

A bromine/nitro moiety linked into the backbone of an ester or other compound over a wide range of occurrence rates provides antimicrobial, bio-resistant and fungal resistant properties for metal working fluids (MWF)s and other coatings. The moiety can be have the bromo and nitro groups linked to the same or different carbon atoms. The present invention also relates to urethanes, urea, amides, imides, carbonates, ethers, siloxanes, and many other types of linkages essential to MWF bases.

5 Claims, 4 Drawing Sheets

ESTERS WITH ANTIMICROBIAL, BIORESISTANT AND FUNGAL RESISTANT PROPERTIES

This is a continuation of application Ser. No. 14/293,054 filed Jun. 2, 2014, now U.S. Pat. No. 8,901,332 issued Dec. 2, 2014 which was a divisional of application Ser. No. 13/741,518 filed Jan. 15, 2013, now U.S. Pat. No. 8,742,151 issued Jun. 3, 2014. application Ser. No. 13/741,518 was a continuation of application Ser. No. 13/351,512 filed Jan. 17, 2012, now abandoned, which was a continuation of application Ser. No. 12/965,252 filed Dec. 10, 2010, now abandoned, which was a divisional of application Ser. No. 12/287,726 filed Oct. 10, 2008, now abandoned, which was a continuation-in-part of application Ser. No. 11/800,569 filed May 7, 2007, now U.S. Pat. No. 7,439,376 issued Oct. 21, 2008, which was a continuation in part of application Ser. No. 10/603,356 filed Jun. 25, 2003, now abandoned, which claimed priority from U.S. Provisional patent application No. 60/392,007 filed Jun. 26, 2002. application Ser. Nos. 14/293,054, 13/741,518, 13/351,512, 12/965,252, 12/287,726, 11/800,569, 10/603,356 and 60/392,007 are hereby incorporated by reference in their entireties. This application also incorporates by reference my patent application Ser. No. 10/350,928 filed Jan. 23, 2003 entitled Polymers with Antimicrobial, Bioresistant and Fungal Resistant Properties in its entirety.

The text of this application is substantially identical to that of grandparent application Ser. No. 10/603,356.

BACKGROUND

1. Field of the Invention

The present invention relates to the field of esters and more particularly to esters with bioresistant, fungal resistant and antimicrobial/antifungal properties.

2. Description of the Problem Solved by the Invention

Due to environmental regulation, the use of tin, mercury, lead, and other heavy metals to control the growth of microbes in organic systems is now prohibited. In particular metal working fluids (MWF) and metal working fluid bases suffer a failure mode when attacked by microbes. The problem is especially acute in water extendable and emulsion MWF systems. The attack of the microbes on the MWF base causes the pH of the system to drop, which destabilizes the emulsion and also increases the corrosion of metal parts that are exposed to the attacked fluid. Aside from the obvious problems that microbes cause in MWFs, operator health issues also arise due to continuous exposure to high levels of bacteria.

Current systems in place include the addition of biocides to the fluid to prevent the bacteria from breaking down the MWF. One common biocide in use is the family of isothiazolinones. This product family is generally hazardous to handle and causes sensitization in many people when exposed repeatedly. The sensitization often takes the form of itching all over the body, or hives when any part is in contact with the isothiazolinone. Additionally, the isothiazolinone family is relatively unstable at the alkaline pH that most MWFs are maintained at. This then requires the operator to add more material on a regular basis. Also, the microbes develop a tolerance to isothiazolinones. This again requires the operator to increase the amount of the isothiazolinone in the system.

A second biocide technology is the use of formaldehyde condensates. These materials are generally hazardous, but do not lead to sensitization of the operators in contact with the MWF. The formaldehyde condensates do contribute to free formaldehyde in the workplace, but the results are not consistent as to how much formaldehyde they contribute to the workplace atmosphere. Most formaldehyde condensates are volatile and evaporate. This requires their replenishment on a regular basis even when they are not consumed.

What is needed is a system that uses an ester as the MWF base that is not susceptible to microbial attack. The material fails to act as a food source for the microbes that are able to digest the current MWF bases.

SUMMARY OF THE INVENTION

The present invention relates to an ester that contains an antimicrobial moiety that is linked into the backbone of the molecule. This moiety is, in general, a bromine atom and a nitro ($NO_2$) group linked to one or more of the carbon atoms forming the backbone of the molecule that is the MWF base. While the present invention is directed primarily to esters, the moiety taught should also be effective when linked onto a carbon atom in the backbone of any suitable MWF base molecule. The moiety can appear in the backbone of the MWF base in various levels of occurrence. A preferred occurrence of around 1000 parts per million on a weight basis is effective; however the frequency of occurrence can be as low as 5 parts per million to as high as 99-100%. MWF base types within the scope of the invention include, but are not limited to urethane, urea, amide, ester, carbonate, ether, and siloxane linkages.

It is well known in the art to combine a carboxylic acid and an alcohol in the presence of a suitable catalyst to form an ester. The present invention adds a bromo-nitro substituted alcohol, diol or polyol to a standard alcohol to be used in the ester synthesis. The proportion of substituted compound used is chosen to yield the desired concentration of the moiety in the final MWF base. A preferred diol for the application is bromonitropropanediol or 2-bromo-2-nitro-propane-1-3-diol or simply BNPD. This particular diol is a solid material with varying degrees of solubility in other alcohols and has proven antimicrobial properties.

In addition, BNPD has been shown to have no tetragenecy (cancer causing effects) and is approved by the CFTA at levels of up to 0.1% for use in cosmetics. BNPD has also been used in baby wipes for its antimicrobial properties.

The fact that the active antimicrobial moiety is covalently linked directly into the backbone of the ester reduces its breakdown at the alkaline pHs required of MWFs. In addition, the moiety is not photo-active or decomposed by sunlight or exposure to mineral salts such as calcium chloride, magnesium hydroxide and sodium chloride as are found in hard and softened water.

Because BNPD is a substituted diol, it is a natural reactant to form part of an ester linkage with a carboxylic acid. Also, being a diol, it mixes directly with a wide range of alcohols or polyols and other performance enhancing additives with no difficulty or adverse reactions. In fact, it can be mixed in any desired proportion (to the extent that it is soluble) with any standard alcohol used in synthesizing esters, ethers, or urethane type linkages.

While bromonitropropanediol (BNPD) is the preferred antimicrobial agent because of its proven activity and its benign effects on the environment and on humans, other alcohols, diols or polyols with bromine and nitro groups linked at the same or different carbon atoms can also be incorporated into the backbone of MWF bases. Any other antimicrobial agents that can be linked onto an alcohol reacted linkage are within the scope of the present invention.

DETAILED DESCRIPTION OF THE INVENTION

Figure 1:
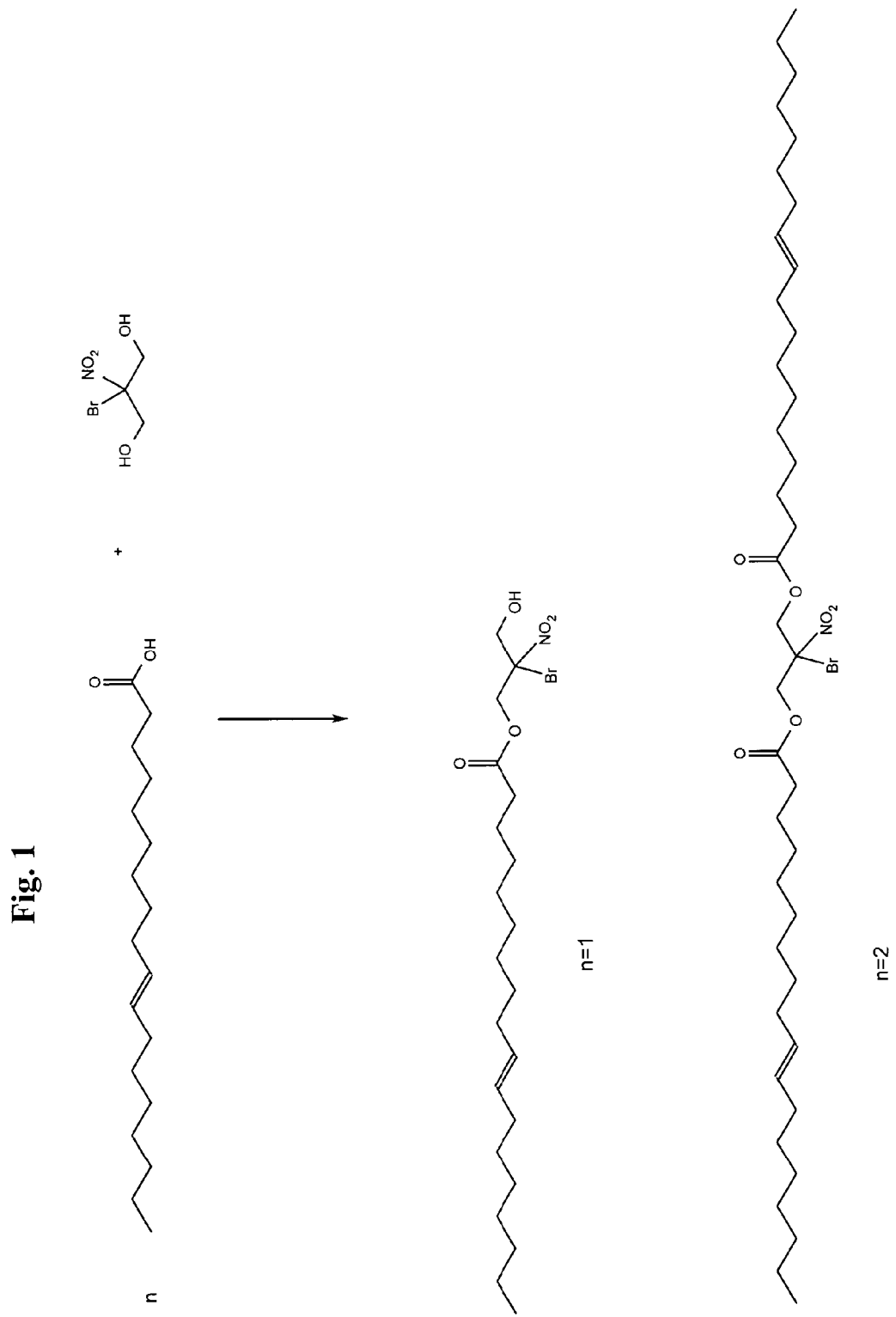
FIG. 1 shows the formation of an ester linkage with BNPD.

It is well known in the art to combine alcohols with carboxylic acids to form ester linkages. One example is isopropyl oleate, the ester of isopropyl alcohol and oleic acid. Polyols are also commonly used, such as in the production of Lexolube 21-214 by Innolex. A typical ester will have the following formula:

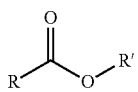

where R typically comes from the original carboxylic acid and R' typically comes from the original alcohol. It is well known in the art that R and R' can be the same or different. The typical example noted above as isopropyl oleate has the following structure:

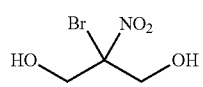

The compound bromonitropropanediol or 2-bromo-2-nitro-propane-1,3-diol (BNPD) has known antimicrobial properties. Tests on this compound have shown that it is effective against various strains of both gram positive and gram negative bacteria in concentrations of 1-50 ppm with the average minimum inhibitory concentration being around 25 ppm. In addition, work has indicated that BNPD is also antifungal. BNPD has the following structure:

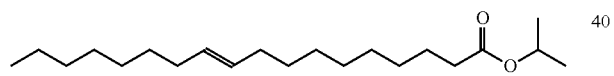

Because BNPD is a polyol, it can be combined with other alcohols, diols, or polyols in the manufacture of the esters used as MWF bases. In particular, BNPD alone or mixed with other alcohols, can be combined with carboxylic acids to form esters that are suitable for use as MWF bases. This causes the active moiety to become covalently linked into the ester. In the case of the oleate ester, the product is:

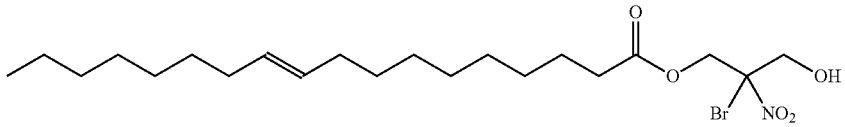 [SMILES: CCCCCCC/C=C/CCCCCCCCC(=O)OCC(Br)(CO)[N+](=O)[O-]]

Or more generally:

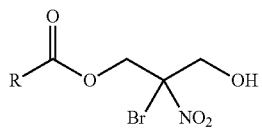

The dioleate ester can easily be made, which has the following structure:

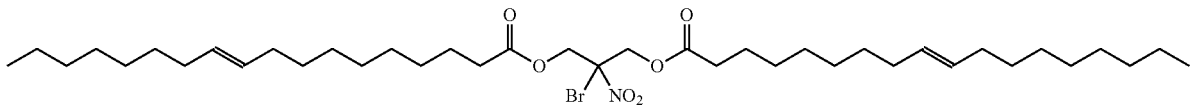 [SMILES: CCCCCCC/C=C/CCCCCCCCC(=O)OCC(Br)(COC(=O)CCCCCCC/C=C/CCCCCCCC)[N+](=O)[O-]]

Or more generally, for the diester:

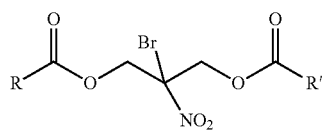

While BNPD is a preferred polyol starting point to link the active moiety into an ester MWF base, it is within the scope of the present invention to use many other materials that contain a bromine atom and nitro group linked near one another. The preferred class of compounds contains the bromine and nitro linked to the same carbon atom; however, it is felt that a moiety where the bromine and nitro are not linked to the same carbon, but near each other will still be effective. Many other similar compounds can also be used. In particular, bromonitromethanediol, bromonitroethanediol, bromo-nitrobutanediol, etc. can also be substituted into molecule backbones with similar results. It should be understood that these are just examples of the many compounds within the scope of the present invention. The prior art has shown that bromonitromethane is effective for the treatment of nematodes in the soil (See U.S. Pat. No. 5,013,762 which is hereby incorporated by reference) and as a general biocide (See U.S. Pat. No. 5,866,511 which is hereby incorporated by reference). It is felt that bromo-nitromethanediol and similar diols are equally effective.

The present invention also includes using a BNPD or BNPD analog as the terminus, such as:

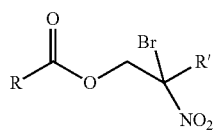

Where R' can be, but is not limited, to CH2OH, OH, CH3, or H.

The present invention reacts BNPD or similar substituted alcohols, diols or polyols, with or without the aid of a solvent or co-solvent, with a carboxylic acid to form the ester MWF base.

The present invention results in a covalently linked bromine/nitro moiety in the backbone of an ester at some frequency of occurrence that provides antibacterial or anti-fungal effects. The present invention relates to ester, urethane, urea, amides, imides, carbonates, ethers, siloxanes, and many other types of linkages essential to MWF bases.

Figure 2:
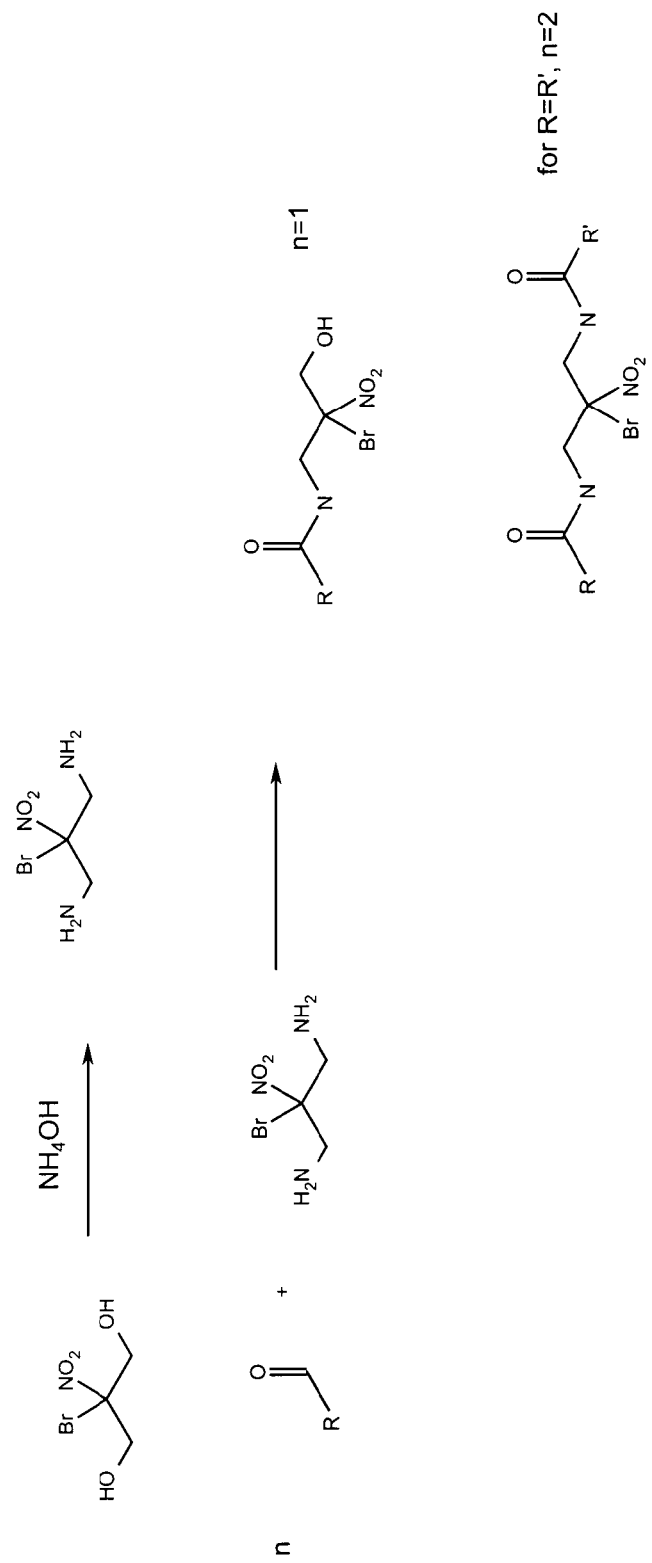
FIG. 2 shows treatment of BNPD with ammonium hydroxide to form an amide.
Figure 3:
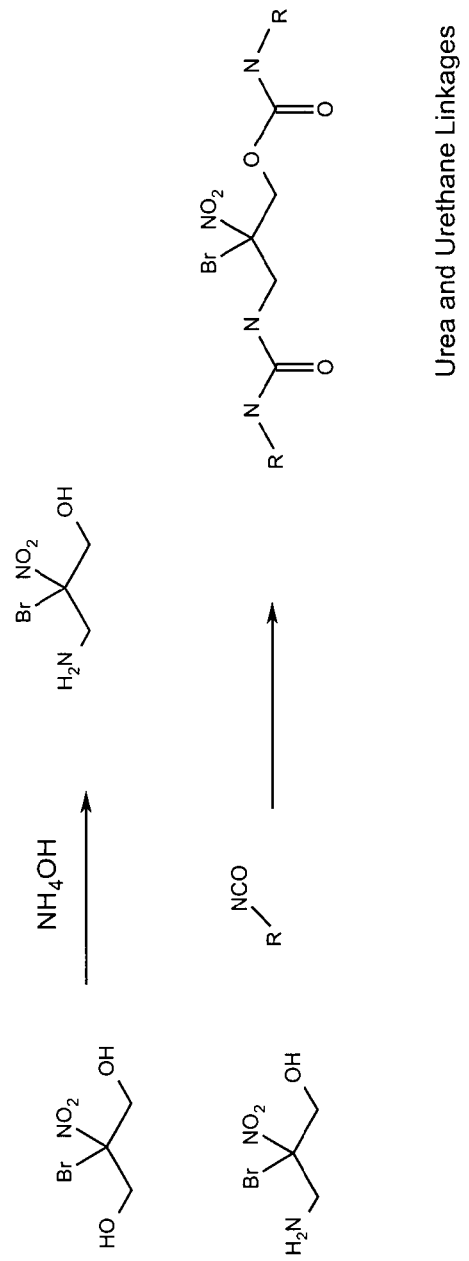
FIG. 3 shows the formation of both urethane and urea linkages.
Figure 4:
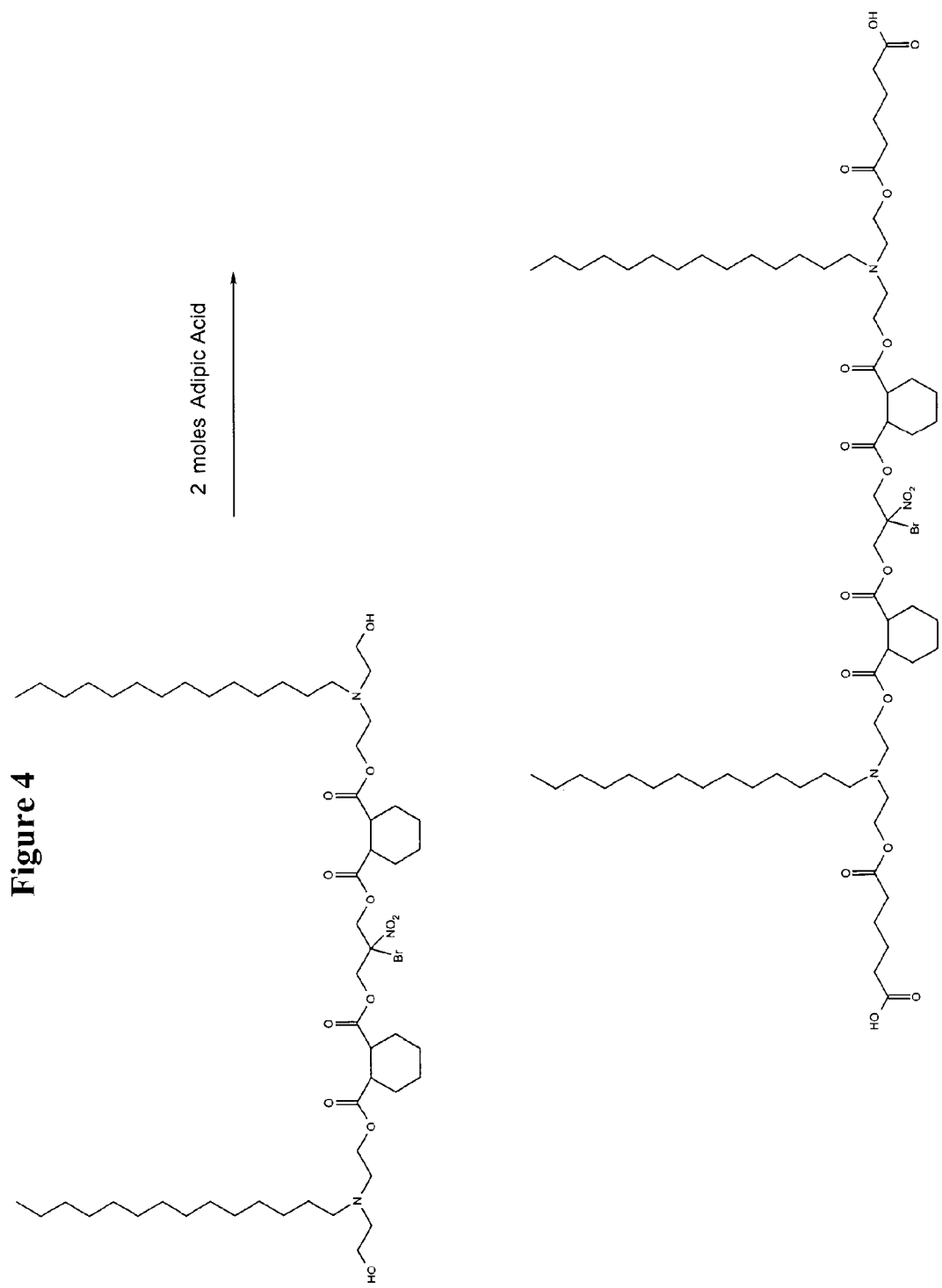
FIG. 4 shows the synthesis of an acid functional, pendant fatty chain.

FIG. 1 shows the formation of an ester linkage with BNPD. FIG. 2 shows treatment of BNPD with ammonium hydroxide to form a bromonitro amine or diamine which can then be combined with an aldehyde or carboxylic acid to form an amide. FIG. 3 shows the formation of both urethane and urea linkages. FIG. 4 shows the synthesis of an acid functional, pendant fatty chain.

The examples and illustrations presented herein are for the purpose of understanding the concepts of the present invention. It will be clear to one with ordinary skill in the art that many other examples and structures are within the scope of the present invention. This applies particularly to classes of linkages where an example of one particular structure has been given; it will be appreciated by one skilled in the art that in such a case, the entire class of compound is within the scope of the present invention.

EXAMPLE 1

Production of a Metal Working Fluid Base

A vessel equipped with a nitrogen blanket and condenser was charged with 1128 g (4 moles) of oleic acid, 400 g BNPD (2 moles) and 2 g conc. Sulfuric acid. The vessel was heated to 288 F when condensation began. The temperature leveled off between 352 F and 356 F and was kept at temperature for 3 hours. The BNPD dioleate recovered was a dark brownish liquid.

The dioleate produced was then incorporated into a standard MWF base at 10% (1,300 PPM BNPD) in the concentrate by substituting it for part of the existing ester. The bases were then subjected to ASTM 3946-92, "Standard Test Method for Evaluating the Bacteria Resistance of Water-Dilutable Metal Working Fluids". On Day 5 of the testing, the BNPD ester containing fluid showed bacterial count of $3\times10^3$ CFU/ml, which is considered under control. The control sample had a bacterial count of $1\times10^7$, which is not considered under control.

At an incorporation level of 6% (823 PPM BNPD) in the standard MWF base a bacterial count of $1.5\times10^4$ CFU/ml was observed after five days of testing. This level is still considered under control and a significant improvement over the $1\times10^7$ CFU/ml observed in the standard MWF base without any BNPD substituted ester.

A slight decrease in wear was also noted with the BNPD substituted products in the pin and v-block tests performed.

EXAMPLE 2

Synthesis of Acid Functional, Pendant Fatty Chain Containing, BNPD Ester

In a vessel with heat, agitation, condenser, and nitrogen blanketing is charged 400 g (2 moles) of BNPD, 616 g (4 moles) of 1,2-Cyclohexanedicarboxylic anhydride (HHPA) and 150 g xylene as a reflux solvent. The vessel is heated to 323 F at which point the reaction exothermed and began to darken. The temperature was then reduced and held at 302 F for one hour. 1162 g of final product was recovered that was a thick, dark transparent liquid. This product will be referred to as HHPA/BNPD-003.

In a vessel with heat, agitation, condenser, and nitrogen blanketing is charged 706 g of HHPA/BNPD-003 from above, 806 g of Crisamine PCD-2, 2 mole ethoxylate of primary coco amine, and 150 g xylene as a reflux solvent. The vessel is heated to 350 F for three hours until the theoretical water loss was collected in the trap and the evolution of water stopped. Approximately 1,400 g of a dark, thick translucent liquid was recovered. This product will be referred to as HHPA/BNPD/coco diol.

In a vessel with heat, agitation, condenser, and nitrogen blanketing is charged 526 g of HHPA/BNPD/coco diol from above, 146 g of adipic acid, and 150 g xylene as a reflux solvent. The vessel is heated to 400 F for 2.5 hours until the theoretical water loss was collected in the trap and the evolution of water stopped. Approximately 600 g of a dark, thick translucent liquid was recovered. The synthesis and structure is shown in FIG. 4.

The invention claimed is:
1. A molecule of the following structure:

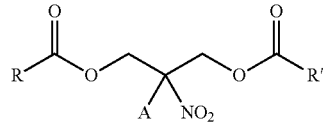

where R and R' are equal or not equal and are polysiloxane or polydimethylsiloxane with molecular weights up to 7000, where A is —CN, —SO3H, or —CH$_2$O(C=O)R" where R" is a saturated or unsaturated, linear or branched alkyl from 2 to 22 carbons.

2. A metal working fluid base comprising a molecule according to claim 1.

3. A surfactant comprising a molecule according to claim 1.

4. A foaming or anti-foaming agent comprising a molecule according to claim 1.

5. A skin conditioning agent comprising a molecule according to claim 1.

* * * * *